United States Patent [19]

Anello et al.

[11] 4,081,487

[45] Mar. 28, 1978

[54] PREPARATION OF 1-CHLORO-2-TRIFLUOROMETHYL-3,3,3-TRIFLUOROPROPENE FROM ISOBUTANE

[75] Inventors: Louis G. Anello, Hamburg; Richard F. Sweeney, Elma; Bernard Sukornick, Williamsville, all of N.Y.

[73] Assignee: Allied Chemical Corporation, Morris Township, N.J.

[21] Appl. No.: 754,386

[22] Filed: Dec. 27, 1976

[51] Int. Cl.$^2$ ............................................. C07C 21/18
[52] U.S. Cl. .............................. 260/653.4; 260/653.3; 260/653.5; 260/653.7
[58] Field of Search ............... 260/653.4, 653.5, 653.7, 260/653.3

[56] References Cited

FOREIGN PATENT DOCUMENTS 1,087,873  10/1967  United Kingdom ............. 260/653.4

Primary Examiner—C. Davis
Attorney, Agent, or Firm—Jay P. Friedenson

[57] ABSTRACT

Isobutane is catalytically converted to 1-chloro-2-trifluoromethyl-3,3,3-trifluor propene [$(CF_3)_2C = CHCl$] in a dehydro/chlorofluorination reaction zone by passing a mixture of anhydrous hydrogen fluoride, chlorine and the isobutane over a chromium oxide or metal fluoride dehydro/chlorofluorination catalyst. Alternatively, the isobutane feed is first prechlorinated, and the mixture of prechlorination fed for conversion to the desired $(CF_3)_2C = CHCl$, to a downstream fluorination reactor charged with the dehydro/chlorofluorination catalyst.

18 Claims, No Drawings

4,081,487

PREPARATION OF 1-CHLORO-2-TRIFLUOROMETHYL-3,3,3-TRIFLUOROPROPENE FROM ISOBUTANE

BACKGROUND OF THE INVENTION

1. Field of the Invention:

The present invention relates to a process for the preparation of 1-chloro-2-trifluoromethyl-3,3,3-trifluoropropene [$(CF_3)_2C = CHCl$] from isobutane, and, more especially, relates to the preparation of 1-chloro-2-trifluoromethyl-3,3,3-trifluoropropene by the catalytic dehydro/chlorofluorination of isobutane.

2. Description of the Prior Art:

1-chloro-2-trifluoromethyl-3,3,3-trifluoropropene is a known compound. This olefin is of value as an intermediate in the preparation of hexafluoroisobutylene. Hexafluoroisobutylene, i.e., 3,3,3-trifluoro-2-trifluoromethyl-1-propene, is a valuable commercial monomer used in the production of a number of polymeric materials. Among such polymers is the copolymer with vinylidene fluoride, the preparation of which is described in U.S. Pat. No. 3,706,723 to Chandrasekeran et al. Hexafluoroisobutylene is presently advantageously prepared from hexafluoroacetone and ketene. See U.S. Pat. No. 3,894,097 to Vanderkooi, Jr., et al. The high costs and limited availability of hexafluoroacetone nevertheless militate against the use of this route for manufacturing commercial quantities of hexafluoroisobutylene. Alternate routes to the preparation of hexafluoroisobutylene are, for example, disclosed or noted in the aforesaid 3,894,097 Vanderkooi, Jr. et al patent, as well as in the U.S. Pat. No. 3,655,786 to Gilbert et al.

The known 1-chloro-2-trifluoromethyl-3,3,3-trifluoropropene has itself been prepared by the chlorofluorination of the olefin isobutylene in the presence of elemental carbon. Compare British Patent Specification No. 1,087,873. Isobutylene has also been non-catalytically chlorofluorinated in an empty tube, as per Canadian Pat. No. 942,323 and U.S. Pat. No. 3,436,430 to Hall. Nonetheless, the procedures disclosed in these patents are unsatisfactory because the yields of product 1-chloro-2-trifluoromethyl-3,3,3-trifluoropropene are low and, for that matter, conducting the procedures outlined at examples 1 and 2 of the 1,087,873 British patent even gives rise to concomitant, massive breakdown to halomethanes.

SUMMARY OF THE INVENTION

It is, therefore, a primary object of the invention to provide a process for the preparation of 1-chloro-2-trifluoromethyl-3,3,3-trifluoropropene from an isobutylene congener which avoids the difficulties and shortcomings of the prior art processes.

Another object of the invention is to provide a process for the preparation of 1-chloro-2-trifluoromethyl-3,3,3-trifluoropropene from the saturated isobutane, wherein the $(CF_3)_2C = CHCl$ is produced in high conversion and in continuous manner.

Yet another object of the invention is to provide a process for the catalytic dehydro/chlorofluorination of isobutane to $(CF_3)_2C = CHCl$ without either concomitant breakdown to halomethanes or carbonization.

These and other objects, features and advantages of the invention will become more apparent from the description which follows.

In accordance with a first embodiment of this invention, isobutane is catalytically dehydro/chlorofluorinated to $(CF_3)_2C = CHCl$ in a single reaction zone by passing a mixture of anhydrous hydrogen fluoride [HF], chlorine and the isobutane over a chromium oxide or metal fluoride dehydro/chlorofluorination catalyst.

According to a second embodiment of the invention, the isobutane feed is first prechlorinated, either in a single step or a multiplicity of steps, and the mixture of prechlorination fed for conversion to the desired $(CF_3)_2C = CHCl$, either directly or indirectly, to a downstream fluorination reactor charged with the chromium oxide or metal fluoride dehydro/chlorofluorination catalyst.

DETAILED DESCRIPTION OF THE INVENTION

In one embodiment of the process according to this invention, anhydrous hydrogen fluoride, chlorine, and isobutane are charged to a reactor and are passed over certain metal dehydro/chlorofluorination catalysts, i.e., chromium oxide or metal fluoride dehydro/chlorofluorination catalysts. The gases exiting from the reactor are then conveyed through suitable product recovery system, e.g., desirably passed through a water scrubber, a caustic scrubber, a drying tower, and finally condensed in a dry ice/acetone cooled trap. A portion of the product mixture is found in the water scrubber, with the remainder being in the dry ice/acetone cooled trap. The organic product in the water trap is next phase separated, dried, and combined with the contents of the cold trap and the desired $(CF_3)_2C = CHCl$ product separated by distillation.

Although the chlorofluorination reactions can be carried out in a single reactor, it is generally preferred to prechlorinate the isobutane and to pass a mixture of chloro-isobutanes and chloro-isobutenes into the fluorination reactor according to a second embodiment of the invention. Prechlorination decreases the amount of breakdown products. The prechlorination can be carried out in a single step or in a plurality of steps. The product of the chlorination step can be passed directly into the fluorination reactor or collected and fed into the fluorination reactor at a later point in time. It is most important that an average of between four and five chlorine atoms be present in the organic molecule fed to the fluorination reactor. A particularly preferred method of achieving this degree of chlorination comprises the use of two chlorination stages. In the first stage, the isobutane and chlorine are advantageously mixed in a tubular reactor at room temperature and then passed into a second heated tubular reactor. The reaction in the first reactor produces an exotherm but no external heating is applied. The contact time in the first reactor desirably ranges from between about 0.01 to 1 second. A contact time of about 0.2 seconds is preferred. The second reactor is heated to about 300° to 400° C. A preferred temperature is about 375° C. The contact time in the second reactor usually varies from between about 1 and 50 seconds, with the preferred contact time being in the range of between about 5 and 20 seconds. The chlorine/isobutane mole ratio desirably varies between about 2:1 to 12:1, with a 4:1 to 6:1 ratio being the preferred. An inert gas stream consisting of nitrogen or helium is generally mixed with the chlorine feed to sweep the reactants through the system. The products of the chlorination reaction may be passed as vapor directly into the downstream fluorination reactor, or condensed and separated from HCl and insufficiently halogenated products by distillation. This collected chlorinated organic may then be revaporized and passed into the fluorination reactor at any later point in time. It is critical that an average chlorine content of at least 4 chlorine atoms per molecule of organic be achieved.

The chlorination reactors are preferably tubular, constructed of material resistant to both chlorine and HCl, with Inconel being particularly preferred.

The chlorination of the isobutane can be conducted either in vapor or in liquid phase. The isobutane and the chlorine, for example, can be passed into and dissolved in a suitable inert solvent contained in a stirred flask, and the chlorination effected by heating, irradiation with light, or catalytically induced such as by stannic chloride, or a variety of combinations of the above.

The dehydro/chlorofluorination or fluorination reaction according to the invention is carried out either in fluidized or fixed bed by passing the organic mixture, together with anhydrous HF and chlorine, into a heated tubular reactor packed with the chromium oxide or metal fluoride dehydro/chlorofluorination catalyst. The reactor is maintained at a temperature of from about 300° to 500° C., with 375° to 450° C. being the preferred. There is a considerable exotherm and the reactor temperature is that which is measured at the hot spot. The contact time desirably ranges from between about 1 and 50 seconds, with 5 to 20 seconds being the preferred range. The chlorine/organic mole ratio is between 1:1 to 20:1, preferably between 3:1 to 7:1. The HF/organic mole ratio is between 2:1 and 20:1, with 4:1 to 10:1 being the preferred range.

One catalyst used in the process according to the invention is chromium oxide, the same being commercially available, for example, from Pfizer Chemical as chipped chromium oxide hydrate. Any off-the-shelf chromium oxide hydrate as received is not in and of itself suitable for use as a dehydro/chlorofluorination or fluorination catalyst without prior conditioning. Such catalyst is conditioned by heating in the presence of an inert carrier gas for from 24 to 48 hours, as the temperature is raised in stages from about 150° to 400° C. At this point the catalyst bed is cooled to about 200° C. Anhydrous HF is then passed over the chromium oxide for 8 to 16 hours as the temperature is next raised in stages to about 400° C. Other conditioning procedures or conditions are equally well adapted to produce a catalyst suitable for use in the process of the invention. In general any one of a number of chromium oxide catalysts are suitable for use in the subject process. Examples of such catalysts are set forth in U.S. Pat. Nos. 2,745,867, 3,235,612, 3,258,500 and 3,413,363. Also effective in the process of the invention is a supported chromium oxide catalyst, e.g. chromium oxide coated into a typical art recognized substrate or support such as carbon, alumina, calcium fluoride, magnesium fluoride, or sodium magnesium fluoride. Similarly, chromium oxide catalyst modified with various metal salts are also within the ambit of this invention; compare, for example, British Patent Specification No. 1,283,386.

The dehydro/chlorofluorination or fluorination reactions can also be conducted over metal fluoride catalysts such as $AlF_3$, $FeF_3$, $KMgF$, $V_2OF_4$, $ZrF_4$, $CoF_2$, $CrF_3$, and the like. Compare, e.g., British Patent Specification No. 823,519 and U.S. Pat. Nos. 2,669,590 and 3,650,987. Preferred are the polyvalent, or transition or Group VIII metal fluorides, and most preferably same are coated onto the art recognized supports, a typical example being the dehydro/chlorofluorination catalyst prepared by coating $FeF_3$ or $CoF_2$ onto activated carbon.

Useful promoters when utilized in conjunction with the subject chromium oxide catalysts are such materials as $NiO$, $Fe_2O_3$, $ZnO$, $Al_2O_3$, $SrO_2$, $Al_2O_3$—$SrO_2$, $TiO_2$ or $AlF_3$—$Al_2O_3$.

In order to further illustrate the invention and the advantages thereof, the following specific examples are given, it being understood that same are intended only as illustrative and in nowise limitative.

EXAMPLE I

Commercially available chromium oxide hydrate chipped catalyst (about 275 cc. of 4–8 mesh pellets) were charged into a 1 inch I.D. × 27 inch long Inconel reactor (fluorinator) mounted in an electrically heated furnace equipped with means for maintaining in the reactor a temperature between 300° and 500° C. The inlet end of the reactor was connected to a 1 inch I.D. × 14 inch long upacked Inconel prechlorinator, also electrically heated. The inlet end of the prechlorinator was provided with facilities for metered introduction of vaporous reactants, and the outlet end to a typical product recovery system. For completion of preparation, or conditioning of the catalyst prior to the use of same, the chromium oxide hydrate pellets in the reactor were heated to 200° and then to 400° C. for about 48 hours or until the heater exit contained no water of dehydration. Thereafter the catalyst was cooled to 200° C. and treated with anhydrous fluoride at 200° to 400° C. for about 16 hours.

Subsequent to catalyst conditioning, temperature in the fluorinator was raised to 425° C. and was so maintained throughout the run. The temperature in the prechlorinator was maintained at 375° C. during the run. Over a period of 6 hours, about 27 g. (0.46 mols) of isobutane, 275 g. (3.87 mols) of chlorine, 103 g. (5.12 mols) of anhydrous HF and 42 liters (1.75 mols) of nitrogen diluent were simultaneously metered into the reactor and through the catalyst bed. The isobutane, $Cl_2$, HF and nitrogen mole ratio are about 1:8:10:1, and the charging of the reactants was such that the contact time in the prechlorinator was about 5 seconds and in the fluorinator was about 10 seconds. About 90 g. of organics were collected in the water and cold traps. The organic condensate was analyzed by glc and 50 area percent of $(CF_3)_2C = CHCl$ was determined to be present.

EXAMPLE II

The reaction system used in this example was similar to that of Example I. The temperature in the fluorinator was maintained at 425° C. and the temperature in the preheater (prechlorinator) was maintained at 300° C. during the run. Over a period of 3 hours, about 108 g. (0.55 mols) of partially chlorinated isobutane derivatives, 189 g. (2.66 mols) of chlorine, 128 g. (6.40 mols) of anhydrous HF and 13 liters (0.55 mols) of helium diluent were simultaneously metered into the reactor and through the catalyst bed. The organic:$Cl_2$:HF:helium mole ratio was about 1:5:11:1, and the contact time was about 5 seconds. About 85.8 g. of organics were collected in the water and cold traps. Excess chlorine collected was 44 g. (0.62 mols). The water scrubber liquor was titrated for total acid and HCl and about 8.26 mole acid and 5.57 mols $Cl^-$ were obtained. The organic condensate was analyzed by glc and 64.68 area percent of (CF$_3$)$_2$C = CHCl was determined to be present. Again assuming area percent to be equivalent to weight percent, 55.5 g. (0.278 moles) of (CF$_3$)$_2$C = CHCl were formed for a 50.5 percent yield.

EXAMPLE III

Following the procedure of Example II, the temperature of the fluorinator was maintained at 325° C. and the temperature of the preheater was maintained at 300° C. during the run. Over a period of 3 hours, about 62 g. (0.32 mols) of partially chlorinated isobutane derivatives, 110 g. (1.55 mols) of chlorine, 67 g. (3.35 mols) of anhydrous HF and 7.7 liters (0.32 mols) of helium diluent were metered into the reactor and through the catalyst bed. The organic:Cl$_2$:HF:helium mole ratio was about 1:5:10:1 and the contact time was about 10 seconds. About 40.5 g. of organics were collected in the water and the cold traps. Excess chlorine collected was 37 g. (0.52 mols). The water scrubber liquor was titrated for total acid and HCl and about 4.55 mols acid and 2.44 mols Cl$^-$ were obtained. The organic condensate was analyzed by glc and 13.75 area percent of (CF$_3$)$_2$C = CHCl was determined to be present. The yield of (CF$_3$)$_2$C = CHCl basis 13.75 area percent reflects that 5.5 g. (0.028 mols) of (CF$_3$)$_2$C = CHCl were formed for a 8.72 percent yield.

EXAMPLE IV

Following the procedure of Example II, the temperature of the fluorinator was maintained at 425° C. and the temperature of the preheater was maintained at 300° C. during the run. Over a period of 6 hours, about 353 g. (1.43 mols) of partially chlorinated isobutane derivatives (obtained via the photochlorination of methallyl chloride as per the following Example V), 382 g. (5.39 mols) of chlorine, 279 g. (13.95 mols) of HF and 33 liters (1.38 mols) of helium diluent were metered into the reactor and through the chromium oxide catalyst bed. The organic Cl$_2$:HF:helium mole ratio was about 1:4:10:1 and the contact time was 5 seconds. About 272.1 g. of organics were collected in the water and cold traps. Excess chlorine collected was 151 g. (2.13 mols). The water scrubber liquor was titrated for total acid and HCl and about 18.40 mols of acid and 11.85 moles of HCl were obtained. The organic condensate was analyzed by glc and 56.14 area percent of (CF$_3$)$_2$C = CHCl was found. The yield of (CF$_3$)$_2$C = CHCl on area percent basis is 154 g. (0.77 mols) or 53.8 percent.

EXAMPLE V

This example relates to the photochemical chlorination of methallyl chloride. Into a 5 liter, 3 neck flask equipped with stirrer, reflux condenser, thermometer, gas dispersing tube, were charged 2455 g. (27.2 mols) of methallyl chloride. During a period of 31 hours at a temperature of 25° to 50° C. with the aid of two 275 watt sunlamps, 7125 g. (100.5 mols) of chlorine were charged into the reactor. There were recovered 2514 g. (69.0 mols) of HCl and 918 g. (13.0 mols) of excess chlorine. Chlorine utilization was 87%. The organic mixture recovered, 6427 g., was purged with nitrogen to remove residual HCl and chlorine. Glc analysis of the organic oil showed the following products to be present:

| Compound | Area % |
|---|---|
| (CH$_2$Cl)$_2$C(CH$_3$)Cl | 1.56 |

-continued

| Compound | Area % |
|---|---|
| (CH$_2$Cl)$_3$CCl | 0.43 |
| (CHCl$_2$)$_2$C(CH$_3$)Cl | 21.55 |
| (CH$_2$Cl)$_2$C(CHCl$_2$)Cl | 25.25 |
| CH$_3$(CCl$_3$)C(CH$_2$Cl)Cl | 7.09 |
| (CHCl$_2$)$_2$C(CHCl$_2$)Cl | 36.19 |
| CCl$_3$(CHCl$_2$)C(CH$_2$Cl)Cl | 6.93 |
| Others | 1.00 |

The calculated average composition of the oil is C$_4$H$_{4.5}$Cl$_{5.5}$.

Thus, the process of this invention provides for the dehydro/chlorofluorination of isobutane over certain metal catalysts, i.e., over chromium oxide or metal fluoride dehydro/chlorofluorination catalysts. Although one and two carbon molecules have been chlorofluoriated over a variety of catalysts, it was unexpected that a C$_4$ compound such as isobutane could be dehydro/chlorofluorinated in this manner without massive breakdown and carbonization. The 1-chloro-2-trifluoromethyl-3,3,3-trifluoropropene is moreover produced in high conversion in a continuous flow vapor or liquid phase operation by the process of the invention.

While there have been shown and described and pointed out the fundamental known features of the invention as applied to the preferred embodiment, those skilled in the art will appreciate that various modifications, changes and omissions in the preparation of 1-chloro-2-trifluoromethyl-3,3,3-trifluoropropene from isobutane illustrated and described can be made without departing from the spirit of the invention. It is the intention, therefore, to be limited only by the scope of the following claims.

What is claimed is:

1. A process for the preparation of 1-chloro-2-trifluoromethyl-3,3,3-trifluoropropene in high yield, comprising catalytically dehydro/chlorofluorinating isobutane in a reaction zone by passing a mixture of hydrogen fluoride, chlorine and the isobutane over a dehydro/chlorofluorination catalyst selected from the group consisting of a chromium oxide and a metal fluoride dehydro/chlorofluorination catalyst.

2. The process as defined by claim 1, wherein the reaction zone is maintained at a temperature of from about 300° to 500° C.

3. The process as defined by claim 2, wherein the reactant contact time in the reaction zone ranges from between about 1 and 50 seconds.

4. The process as defined by claim 3, wherein the chlorine/isobutane mole ratio ranges from between 1:1 to 20:1.

5. The process as defined by claim 4, wherein the hydrogen fluoride/isobutane mole ratio ranges from between 2:1 to 20:1.

6. The process as defined by claim 5, wherein the dehydro/chlorofluorination catalyst is chromium oxide.

7. The process as defined by claim 5, wherein the dehydro/chlorofluorination catalyst is a polyvalent metal fluoride.

8. The process as defined by claim 5, wherein the dehydro/chlorofluorination catalyst is a transition metal fluoride.

9. The process as defined by claim 1, wherein the dehydro/chlorofluorination catalyst is borne by a support selected from the group consisting of carbon, alumina, calcium fluoride, magnesium fluoride and sodium magnesium fluoride.

10. The process as defined by claim 6, wherein the chromium oxide catalyst further includes a metal salt modifier.

11. The process as defined by claim 6, wherein the chromium oxide catalyst further includes a metal oxide promoter, said metal being other than chromium.

12. The process as defined by claim 6, wherein the chromium oxide catalyst is dehydrated chromium oxide hydrate.

13. The process as defined by claim 1, wherein the reaction zone is maintained at a temperature of from about 375° to 450° C., the reactant contact time in the reaction zone ranges from between about 5 and 20 seconds, the chlorine/isobutane mole ratio ranges from between 3:1 to 7:1, and the hydrogen fluoride/isobutane mole ratio ranges from between 4:1 to 10:1.

14. The process as defined by claim 1, wherein the reaction zone effluent is conveyed through a product recovery system including a water scrubber, a caustic scrubber, a drying tower and a cold trap.

15. The process as defined by claim 1, wherein the catalyst is a metal fluoride selected from the group consisting of $AlF_3$, $FeF_3$, $KMgF$, $V_2OF_4$, $ZrF_4$, $CoF_2$ and $CrF_3$.

16. The process as defined by claim 11, wherein the promoter is selected from the group consisting of NiO, $Fe_2O_3$, ZnO, $Al_2O_3$, $SrO_2$, $Al_2O_3$—$SrO_2$, $TiO_2$ an $AlF_3$—$Al_2O_3$.

17. The process as defined by claim 9, wherein the dehydro/chlorofluorination catalyst is $FeF_3$ coated onto a carbon support.

18. The process as defined by claim 9, wherein the dehydro/chlorofluorination catalyst is $CoF_2$ coated onto a carbon support.

* * * * *